(12) United States Patent
Fazio et al.

(10) Patent No.: US 7,354,759 B2
(45) Date of Patent: Apr. 8, 2008

(54) DNA VACCINES EXPRESSING HYPERVARIABLE VH-CDR3 IDIOTYPIC DETERMINANTS

(75) Inventors: Vito M. Fazio, Rome (IT); Giuseppe Saglio, Turin (IT)

(73) Assignee: Keryos SpA, Milan (IT)

( * ) Notice: Subject to any disclaimer, the term of this patent is extended or adjusted under 35 U.S.C. 154(b) by 483 days.

(21) Appl. No.: 10/466,347

(22) PCT Filed: Jan. 15, 2001

(86) PCT No.: PCT/IT01/00014

§ 371 (c)(1),
(2), (4) Date: Dec. 8, 2003

(87) PCT Pub. No.: WO02/055559

PCT Pub. Date: Jul. 18, 2002

(65) Prior Publication Data

US 2004/0109849 A1 Jun. 10, 2004

(51) Int. Cl.
*C12N 15/63* (2006.01)
*C12N 15/85* (2006.01)
*A61K 48/00* (2006.01)

(52) U.S. Cl. ............... 435/320.1; 435/455; 514/44

(58) Field of Classification Search ......... 435/320.1, 435/455; 514/44
See application file for complete search history.

(56) References Cited

FOREIGN PATENT DOCUMENTS

WO WO-95/05853 A1 3/1995

OTHER PUBLICATIONS

Rinaldi et al. (1998) Gene Ther. Canc., vol. 451, 323-330.*
Raaphorst et al. (1996) Biotechniques, vol. 20 (1), 78, 80-87.*
Ramasamy et al. (1992) J. Clin. Pathol., vol. 45, 770-775.*

Syrengelas A D et al.: "DNA Immunization Induces Protective Immunity Against B-Cell Lymphoma"; Nature Medicine, Nature America, New York, US.; vol. 2, No. 9, Sep. 1996; pp. 1038-1041, XP 000996399.

Stevenson F K et al.: "Idiotypic DNA Vaccines Against B-Cell Lymphoma"; Immunological Reviews, Munksgaard, XX, vol. 145, Jun. 1, 1995, pp. 211-228, XP 000670867.

Rinaldi M. et al.; "Startegies to Elicit Anti-Idiotypic Immune Response in B-Lymphoma Patients: Peptide and Genetic Immunization"; Adv. Exp. Med. Biol., vol. 451,—1998, pp. 323-330, XP 001005261.

Wen Y.J. et al.;"In-Vivo Immune Responses to Idiotypic VH Complementarity-Determining Region 3 Peptide Vaccination in B-Cell Non-Hodgkins Lymphoma"; Brit. J. of Haematology, vol. 103, No. 3, Dec. 1998; XP 001005275.

Campbell M J et al.; "Immunotherapy of Established Murine B Cell Lymphoma. Combination of Idiotype Immunization and Cyclophosphamide"; Journal of Immunology, US, The Williams and Wilkins Co. Baltimore; vol. 141, No. 9, Nov. 1, 1998, pp. 3227-3233; XP 002036673.

Xiong S et al; "Engineering Vaccines With Heterologous B and T Cell Epitopes Using Immunoglobulin Genes"; Nature Biotechnology, Nature Pub. Co., New York, NY, US; vol. 15, No. 9, Sep. 1997, pp. 882-886; XP 000918882.

Irvine K R et al; "Cytokine Enhancement of DNA Immunization Leads to Effective Treatment of Established Pulmonary Metastases"; Journal of Immunology, US, The Williams and Wilkins Co., Baltimore; vol. 156, 1996, pp. 238-245; XP 002030631.

Rinaldi, et al., Antibodies Elicited by Naked DNA Vaccination against the Complementary-determining Region 3 ypervariable Region of Immunoglobulin Heavy Chain Idiotypic Determinants of B-lymphoproliferative Disorders Specifically React with Patients' TumorCells[1]. *Cancer Research 61*, Feb. 12, 2001, pp. 1555-1562.

* cited by examiner

*Primary Examiner*—Anne M. Wehbe
(74) *Attorney, Agent, or Firm*—Darby & Darby P.C.

(57) ABSTRACT

The present invention relates to a method for inducing the immune response of an individual against B-lymphoproliferative disorders. The method is based on DNA vaccination with the short peptide encompassing the CDR3 hypervariable region of immunoglobulin heavy chain (VH-CDR3) alone or in combination with at least another immunomodulating sequence.

18 Claims, 5 Drawing Sheets

Fig. 1.A

Fig. 1.B

Figure 1:
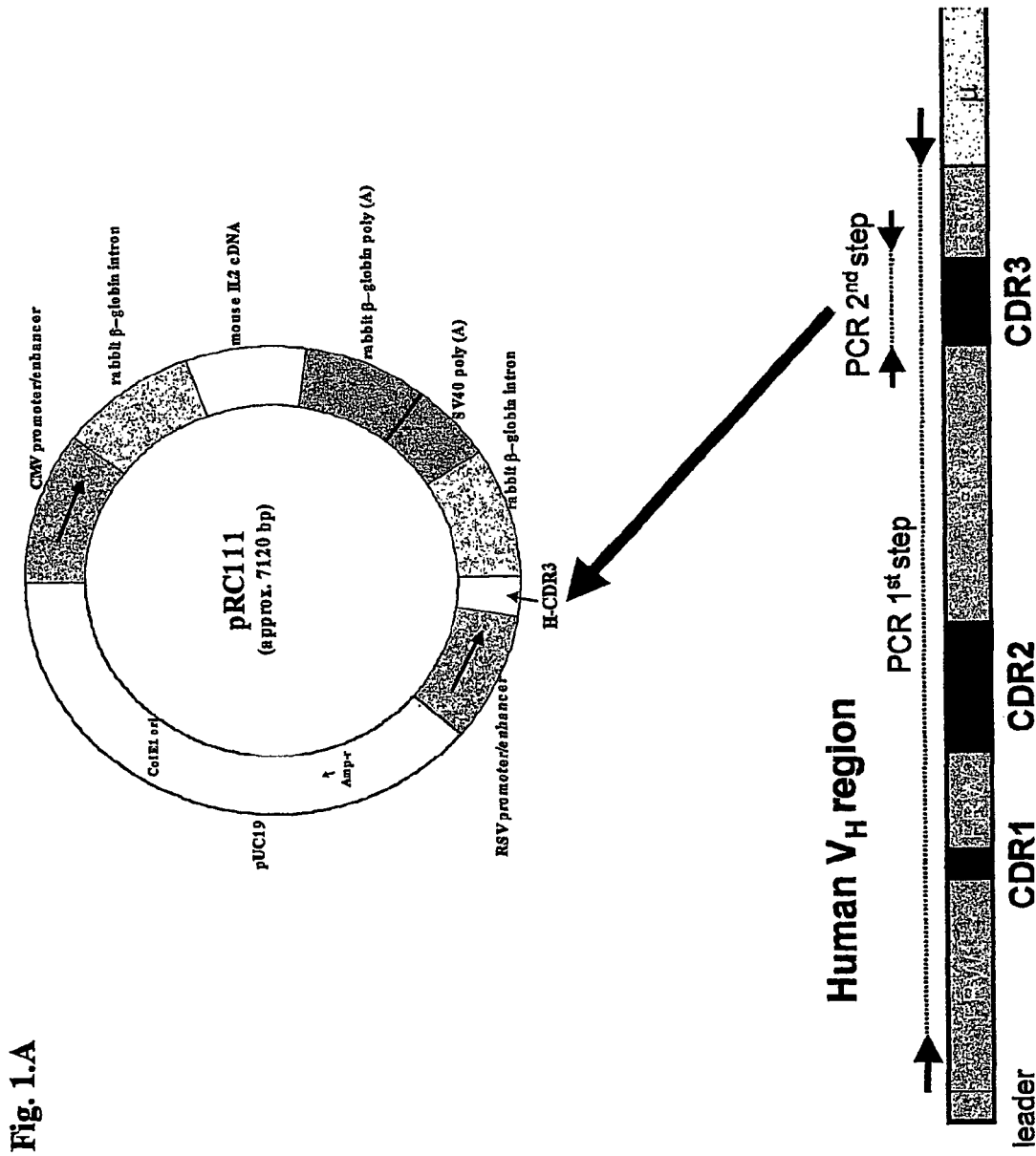

First step primers:

Back:
- VH₁,₃,₅,₇  5'- (C,G)AG GTG CAG CTG GTG (C,G)AG TCT -3'
- VH₂        5'- CAG (G,A)TC ACC TTG AAG GAG TCT -3'
- VH₄        5'- CAG GTG CAG CTG CAG GAG TCG -3'
- VH₆        5'- CAG GTA CAG CTG CAG CAG TCA -3'

Forward: RHm  5'- CAC GCT GCT CGT ATC CGA CGG -3'

Second step primers:

Back: eFW₃  5'-TTT G/CTAGC ATG CAC ACG GC(C,T) (G,C)TG TAT TAC TGT-3'
                    Nhel Forward: eJH  5'-TAT GC/GGCCGC TTA TTA TGA GGA GAC GGT GAC C-3'
                     Notl

Fig. 2

A) CDR3H- sequence (Hairy Cell Leukemia)

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| M | H | T | A | V | Y | Y | C | A | R | V | L | Y | Y |
| ATG | CAC | ACG | GCT | GTG | TAT | TAC | TGT | GCG | AGA | GTT | TTG | TAT | TAC |

| 15 | 16 | 17 | 18 | 19 | 20 | 21 | 22 | 23 | 24 | 25 | 26 | 27 | 28 |
|----|----|----|----|----|----|----|----|----|----|----|----|----|----|
| D | F | W | S | G | Y | Y | I | S | N | Y | Y | Y | Y |
| GAT | TTT | TGG | AGT | GGT | TAT | TAT | ATT | TCT | AAT | TAC | TAC | TAC | TAC |

| 29 | 30 | 31 | 32 | 33 | 34 | 35 | 36 | 37 | 38 | 39 | 40 | 41 | 42 |
|----|----|----|----|----|----|----|----|----|----|----|----|----|----|
| Y | G | M | D | V | W | G | Q | G | T | T | V | T | V |
| TAC | GGT | ATG | GAC | GTC | TGG | GGC | CAA | GGG | ACC | ACG | GTC | ACC | GTC |

| 43 | 44 |
|----|----|
| S | S |
| TCC | TCA |

B) CDR3H- sequence (non-Hodgkin's B-lymphoma)

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| M | H | T | A | V | Y | Y | C | A | R | N | K | D | D |
| ATG | CAC | ACG | GCT | GTG | TAT | TAC | TGT | GCG | AGA | AAT | AAG | GAC | GAT |

| 15 | 16 | 17 | 18 | 19 | 20 | 21 | 22 | 23 | 24 | 25 | 26 | 27 | 28 |
|----|----|----|----|----|----|----|----|----|----|----|----|----|----|
| D | S | P | L | E | Y | W | G | R | G | T | L | V | T |
| GAC | TCC | CCT | CTT | GAG | TAC | TGG | GGC | CGG | GGA | ACC | CTG | GTC | ACC |

| 29 | 30 | 31 |
|----|----|----|
| V | S | S |
| GTC | TCC | TCA |

C) CDR3H- sequence (non-Hodgkin's B-lymphoma)

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| M | H | T | A | V | Y | Y | C | A | K | G | A | Q | G |
| ATG | CAC | ACG | GCT | GTG | TAT | TAC | TGT | GCG | AAG | GGT | GCG | CAG | GGC |

| 15 | 16 | 17 | 18 | 19 | 20 | 21 | 22 | 23 | 24 | 25 | 26 | 27 | 28 |
|----|----|----|----|----|----|----|----|----|----|----|----|----|----|
| A | S | L | G | K | A | Y | F | F | D | C | W | G | Q |
| GCA | TCA | CTT | GGT | AAG | GCC | TAC | TTC | TTT | GAC | TGC | TGG | GGC | CAG |

| 29 | 30 | 31 | 32 | 33 | 34 | 35 | 36 |
|----|----|----|----|----|----|----|----|
| G | T | Q | V | T | V | S | S |
| GGA | ACC | CAG | GTC | ACC | GTC | TCC | TCA |

DNA VACCINES EXPRESSING HYPERVARIABLE VH-CDR3 IDIOTYPIC DETERMINANTS

This is a U.S. national phase application under 35 U.S.C. §371 of International Patent Application No. PCT/IT01/00014, filed Jan. 15, 2001. The International Application was published in English on Jul. 18, 2002 as WO 02/055559 A1 under PCT Article 21(2).

The present invention relates to a method for inducing the immune response of an individual against B-lymphoproliferative disorders; the method is based on DNA vaccination with the short peptide encompassing the CDR3 hypervariable region of immunoglobulin heavy chain (VH-CDR3) alone or in combination with at least another immunomodulating sequence.

BACKGROUND OF THE INVENTION

B cell lymphomas are neoplasms of mature lymphocytes which generally express immunoglobulin (Ig) on the cell surface. The Igs are clone specific and the variable regions contain determinants which may themselves be recognized as antigens or idiotypes. The idiotypic Ig therefore represents a unique tumor-specific antigen. (Wen Y J., et al. Eur. J. Immunol. 1997. 27: 1043-1047). Traditional treatments, such as chemotherapy and radiation therapy, can both induce remission in patients with low grade non-Hodgkin's lymphoma (NHL). However, despite this responsiveness to treatment, the majority of patients ultimately relapse and cannot be cured with these standard therapies and long-term outlook for this patients remains poor.

It is likely that the disease is essentially incurable, except may be by allogenic bone marrow transplantation. As the number of patients who would be suitable for such a therapeutic modality is extremely small, alternative methods of treatment are needed. An attractive approach would be to evoke the ability of the immune system to recognize and eliminate neoplastic cells while sparing normal cells. B-cell lymphomas represent ideal models for experimental tumor immunotherapy. In fact the Ig's idiotypes displayed on their cell surface represent attractive tumoral antigens since they are tumor-specific, belong to a well known family of molecules and it has been demonstrated that idiotype-specific immune response can be obtained also for self Igs. However, the efficacy of the anti-idiotypic vaccination is likely to be more effective in some histotypes than in others. Low grade B-cell lymphomas, as those with a small lymphocytic or follicular histotype, are expected to represent ideal targets because they i) generally show an indolent behaviour and are difficult to eradicate; ii) present a very low degree of clonal evolution; iii) express surface Igs at high levels; iiii) do not secrete surface immunoglobulins.

On the other hand, anti-idiotypic vaccination is expected to be less effective against lymphoblastoid and other high-grade lymphomas, which do not express immunoglobulins on the surface; moreover, these types are very aggressive and may show a high degree of clonal evolution (30-40%).

Although the traditional approach to immunization, i.e., sub-cutaneous immunization with the whole immunoglobulin by B-cell lymphoma mixed with adjuvant, was proven to be effective both in experimental models (George et al. J. Immunol., 138: 2168-2174, 1988), as well as in controlled clinical trials (Kwak et al. N. Engl. J. Med., 327: 1209-1215, 1992), such an approach was hampered by the need of the high amounts of purified protein that have to be prepared and certified for each case.

Several reports have indicated that the immunodominant epitopes of the clone specific Ig lies within the hypervariable regions and mainly within the third complementary determining region of immunoglobulin heavy chain (VH-CDR3) (Campbell et al. J. Immunol., 139: 2825-2833, 1987/Watanabe et al. J. Immunol., 151: 2871-2876, 1993). Furthermore, many observations suggest that immunization with whole protein may in some case produce an antibody response restricted to short linear epitopes, and consequently inadequate, rather than recognizing the three-dimensional structure of the protein itself (Kawaguchi et al. J. Biol. Chem., 264: 5762-5767, 1989). Conversely, immunization with short peptides (8-20 aa residues long) can result in production of antibodies that recognize the corresponding linear epitope on a protein without need for conjugation to carriers, provided that the short peptide behaves as a complete antigen (i.e. contains sequences able to bind Class II MHC molecules and to engage the T-cell receptor).

Indeed, it was demonstrated that a short peptide encompassing the VH-CDR3 region of a human lymphoma specific IgM was able to promote the in vitro proliferation of specific CD4+ and CD8+ cells, capable to lyse the autologous lymphoma cells (Wen et al. Eur. J. Immunol., 27: 1043-1047, 1997). The clinical relevance of these results obtained in vitro was confirmed by the specific immune response obtained in a patient following vaccination with the peptide (Wen et al. Br. J. Haematol., 103: 663-668, 1998).

The development of the method of vaccination by means of direct injection of naked DNA into the muscle or subcutaneously, combined with the ability of easily identifying and cloning individual tumor-specific idiotypes, has improved the chances of exploiting these tumor antigens. This approach has already proven effective in inducing immune responses to several antigens mainly of viral origin, and it has been applied to therapy of experimental murine lymphomas where the Ig characterizing the lymphoma has been used for immunotherapy of the parental tumor via DNA based vaccination (Hawkins et al. Blood, 83: 3279-3288, 1994/Fazio V. M. Res. Virol., 148: 101-108, 1997/Stevenson et al. Immunol. Rev., 145: 211-228, 1995). Such a method has proven effective in eliciting anti-idiotype specific immune responses when whole Ig, or its variable regions engineered to be expressed on non-self Ig (Syringelas et al. Nature Med., 2: 1038-1041, 1996), germ-line light chains (Watanabe et al. J. Immunol., 151: 2871-2876, 1993) or toxin fusion protein (King et al. Nature Med., 11: 1281-1286, 1998) were used as encoded antigen.

Nevertheless, if this technology were to be transferred to clinical practice, such a time consuming work would still be needed for each patient to render this approach too expensive to be carried out on a regular clinical basis.

An efficient and cheap DNA-based method for inducing an immune response against B-lymphoproliferative disorders would be desirable; in particular if we consider that purified double strand DNA itself is not immunogenic (Parker S E, Borellini F. et al. Hum. Gene Ther., 10 (5): 741-58, 1999). Moreover, if we consider that the calculate rate of mutation would be 3000 times less than spontaneous mutation rate for mammalian genomes, the level of integration, if should occur, would not be considered to pose a significant safety concern. (Martin T., Parker S E, et al. Hum. Gene Ther. 10 (5): 759-68).

DESCRIPTION OF THE INVENTION

It has now surprisingly been found that an efficient, safe and easily reproducible DNA-based immune response against B-lymphoproliferative pathologies can be achieved upon administration to the patient of a plasmid containing a DNA sequence essentially coding for a short peptide encompassing the hypervariable region of idiotypic immunoglobulin heavy chain (VH-CDR3).

It has also been found that a multi-gene expression vector, whose principal characteristic is the coexistence of two distinct, complete and differentially regulated transcription units, allowing the co-expression of an immunomodulatory molecule, preferably human interleukin-2 (IL2), and of the CDR3 hypervariable region of idiotypic immunoglobulin heavy chain, remarkably increases the above-mentioned immune response.

The main object of the present invention is therefore represented by the use of the DNA sequence coding for the hypervariable region (VH-CDR3) of the idiotypic immunoglobulin expressed on B-cells of chronic B-lymphoproliferative disorders as a vaccine (or for the manufacture of a vaccine composition), said vaccine being effective against chronic B-lymphoproliferative disorders expressing the surface idiotypic immunoglobulin in mammalians.

According to a preferred embodiment of the invention, said DNA sequence codes for peptides having a length of 0-45 a.a., preferably of 7-45 a.a.; said DNA sequence is comprised between eFW3 and eJH sequences and corresponds to VH-CDR3 sequence.

A second object of the invention is represented by a recombinant plasmid expression vector suitable for expression of a DNA sequence in a mammalian and containing a DNA sequence operably linked thereto, characterized in that said DNA sequence essentially consists of the hypervariable region (VH-CDR3) of the idiotypic immunoglobulin expressed on B-cells of chronic B-lymphoproliferative disorders in a mammalian; as above indicated such a sequence is usually of 745 a.a.

The plasmid which can be used for the purposes of the present application can be selected from multigenic vectors which incorporate two different transcription cassettes controlled by two indipendent promoters, preferably CMV and RSV promoter/enhancers, and allow co-expression of a cytochine or a immunotoxin, such as as human IL-2, GM-CSF or IL-6, together with a specific antigen, namely the individual VH-CDR3 peptide.

According to an embodiment of the invention, said recombinant plasmid expression vector encodes also for an immunomodulatory molecule which can be for instance selected from IL-2, GM-CSF, IL-12, IL-6, or for a fragment from bacterial immunotoxins such as the tetan toxin.

According to a further embodiment of the invention, said DNA sequence consists of: (a) the gene coding for the hypervariable region (VH-CDR3) of the idiotypic immunoglobulin expressed on B-cells of chronic B-lymphoproliferative disorders and (b) upstream and downstream PCR primers; preferably, said upstream PCR primer is eFW3 whereas said downstream PCR primer is eJH.

A third object of the invention is then represented by a vaccine composition containing such a recombinant plasmid expression vector, said vaccine composition being preferably in a form suitable form being administered parenterally, more preferably intramuscularly, such for instance a water solution. The investigation which permitted to make the present invention addressed the question of whether different short peptides encompassing the VH-CDR3 hypervariable region of the lymphoma/leukemia surface immunoglobulin usually, but not limited, between 7-45 aa., expressed by direct intramuscular injection of the corresponding minigenes, might be efficiently presented to the immune system of different outbred mouse, to generate antibodies able of reacting with patient's tumor cells exposing the specific idiotypic protein; the xenogenic, outbred mouse model was decided to mimic the MHC-1 variability present in a clinical setting without immunizing human subjects.

Restriction to the individual CDR3 region excluded xenogenic or allogenic epitopes contained in the variable as well as in the constant region of the idiotypic immunoglobulin, greatly enhancing the safety margin when this approach is transferred in a syngenic context.

A double-gene plasmid vector for the co-expression of the specific individual CDR3 sequences and of an immunomodulating cytokine, i.e. IL-2, was selected as the vehicle for the intramuscular injection.

Such a vector was deemed to improve the safety by linking the expression of the cytokine to the expression of the foreign antigen in the same cells; this strategy ensures in fact the production of the immuno-modulating molecule only when and where needed, that is as long as the foreign antigen itself is produced. It was believed that it would have been unlikely that T cells responsive to a protein (IL2), that is involved in all immune responses and is present at high concentration any time T cells are activated, could survive the induction of tolerance.

As a matter of fact, to our knowledge, there was only one report showing the possibility to induce anti-IL-2 antibodies in mice, but the protocol required immunization with a form of the IL-2 that was truncated and contained amino acid substitution (Matesanz et al: Autoimmunity, 12: 221-227, 1999).

It was thus found that up to 60% of outbred animals injected with each VH-CDR3/IL2 co-expressing plasmid vectors mounted a significant, rapid immune response that lasted at least for 19 weeks after the first DNA injection. The number of responding animals declined up to 20% in the absence of IL2 co-stimulation. More importantly, all VH-CDR3 immune animals developed antibody response able to recognize the entire idiotypic immunoglobulin exposed on the patient-derived lymphoma/leukemia-cells, as demonstrated by FACS analysis.

No cross reactivity was found when immune sera of each VH-CDR3 were challenged with tumor cells of other patients. A possible interpretation of these results is that DNA vaccination by VH-CDR3 linear short peptides may induce production of antibodies which identify specific linear epitopes on the folded idiotypic immunoglobulin.

The currently accepted mechanism of DNA vaccination by intramuscular plasmid injection suggests that the priming is performed by bone marrow-derived antigen-presenting cells (APC), which are efficient at providing all of the necessary signals for priming the T cells. The muscle cells participate in the immunization mechanism as a reservoir for the antigen and a persisting immune stimulus, due to the long-term stability of muscle fibers and transgene expression. The method of DNA vaccination and the form of DNA-expressed antigen may bias T-cell help to primarily type-1 or type-2.

The proposed experimental model includes both intramuscular injection and non secreted peptides which may direct the response to the Th1 pathway. Moreover, IL2 expression may function by enhancing T-cell-mediated immune response and by improving antigen specific T cell proliferation, as well as differentiation and Ig secretion of antigen-activated B-cells.

In this context, antibody response may be generated by B-cell stimulation obtained by peptides released from muscle cells during immune-mediated destruction of transfected muscle fibers.

Several reports suggested that the mechanism of protection against low grade lymphoma is likely to be antibody-mediated (Dyke et al. Cell. Immunol., 132: 70-83, 1991), possibly due to direct induction of apoptosis (Vitetta et al. Blood, 89: 4425-4436, 1997). Very recently experimental data confirmed that tumor-protective effects of DNA vaccination can be mainly ascribed to idiotype-specific humoral immunity (Syrengelas et al. J. Immunol., 1162: 4790-4795, 1999), and still more convincingly prolonged survival in a clinical trial has been correlated with the induction of anti-idiotypic antibody responses.

However, the nature of a protective immune-response in already established low-grade B-cell lymphomas is still debated and other studies call for a correlation between cell-mediated cytotoxicity and therapeutic response (Nelson et al. Blood, 88: 580-589, 1996). In this outbred experimental model the idiotypic peptides are neither secreted nor intravenously injected, but directly produced without specific signals (i.e., leader sequence for secretion) in in vivo transfected cells, in combination with recombinant IL2 expression.

This mechanism may warrant for antibody production and cytotoxic response, without the impairment associated with the binding of anti-idiotypic VH-CDR3 antibodies to the secreted peptide or to the injected peptidic vaccine.

Even if the VH-CDR3 region of the idiotypic immunoglobulin is most variable and therefore most likely to be unique to this protein, most of the somatic mutations that may develop under the immune pressure are clustered in the CDR1, CDR2 and framework 3 (FR3) regions of the idiotypic protein. (Berek C., Milstein C. Immunol. Rev. 96: 23-41.1987).

Due to the ease in identifying new VH-CDR3 idiotypic variants as well as in rapidly cloning and manufacturing clinical-grade DNA vaccine preparations, the proposed protocol may anyway be re-applied in the follow-up of the treated patient.

In conclusion, the immune responses generated by naked DNA immunization in an outbred animal model prove the potential immunogenicity and a large margin of safety of the VH-CDR3 mini-gene encoded peptides, and provide the basis for the vaccination of human patients affected by B-lymphoproliferative disease. This approach in fact avoids xenogenic or allogenic epitopes contained in the variable as well as in the constant region of the idiotypic immunoglobulin, enhancing the safety margin of this molecular approach.

Moreover, the xenogenic outbred experimental model can more closely reproduce the patient setting and the immune response variability, because it mimics the MHC-1 variability present in a clinical setting without immunizing directly human subjects.

According to this invention, it will be now possible to vaccinate humans affected by B-lymphoproliferative disorders by (i) isolating the patient's DNA sequence coding for the hypervariable region (VH-CDR3) of the idiotypic immunoglobulin expressed on B-cells (ii) cloning said sequence into the mentioned expression plasmid (iii) administering the so obtained recombinant expression plasmid to the patient, preferably via intramuscolar injection.

These and other aspects of the present invention will be clarified by the following experimental portion, whose purpose is to illustrate the invention without constituting a limitation of the field of application thereof.

LEGEND

For the purposes of the present application the following abbreviations have been used: CDR3, complementary determining region 3; Ig, immunoglobulin; VH, variable immunoglobulin heavy chain; mIL2, mouse interleukin-2; FRW, framework; GM-CSF, granulocyte-macrophage colony stimulating factor, WBC, white blood cells.

FIGS. 1(A-B): Outline of the experimental strategy. Molecular rescue of VI-I-CDR3 sequences was accomplished from patient tumor B-cells of different chronic lymphoproliferative disorders. Amplified sequences, using first step back primers $VH_{1-3-5-7}$ (SEQ ID NO:17), $VH_2$ SEQ ID NO:16, $VH_4$ SEQ ID NO:15, $VH_6$ SEQ ID NO:14 and forward primer RHm SEQ ID NO:13. Second step back primer eFW3 (SEQ ID NO:12) and forward primer eJH SEQ ID NO:11 were also used to amply sequences. (FIG. 1B) The amplified sequences were cloned into a mammalian multigenic vector (pRC111) (FIG. 1A) which independently co-expresses interleukin-2 and tumor-specific VH-CDR3 sequences. pRC111 vectors containing cloned VH-CDR3 sequences were injected in outbred mice. Sera obtained at different time-points after DNA injection were challenged with the original patients' tumor B-cells and tested by FACS analysis.

Figure 2:
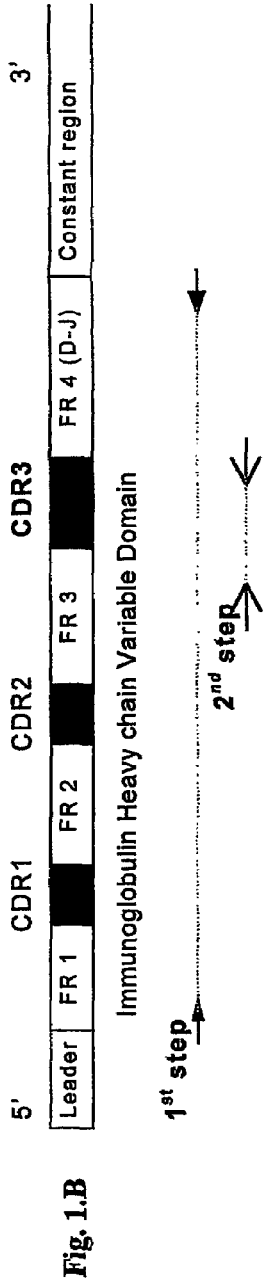

FIGS. 2(A-C): Nucleotide (upper case) and deduced amino acid (single upper case letter) sequence of cDNA encoding human heavy chain CDR3 variable regions from 3 different patients (FIG. 2A): Hairy Cell Leukemia (amino acid SEQ ID NO:6 and nucleotide SEQ ID NO:3); FIG. 2B): non-Hodgkin's B-lymphoma (amino acid SEQ ID NO:5 and nucleotide SEQ ID NO:5); FIG. 2C): non-Hodgkin's B-lymphoma (amino acid SEQ ID NO:1 and nucleotide SEQ ID NO:4). Bold: part of the primer sequences.

Figure 4:
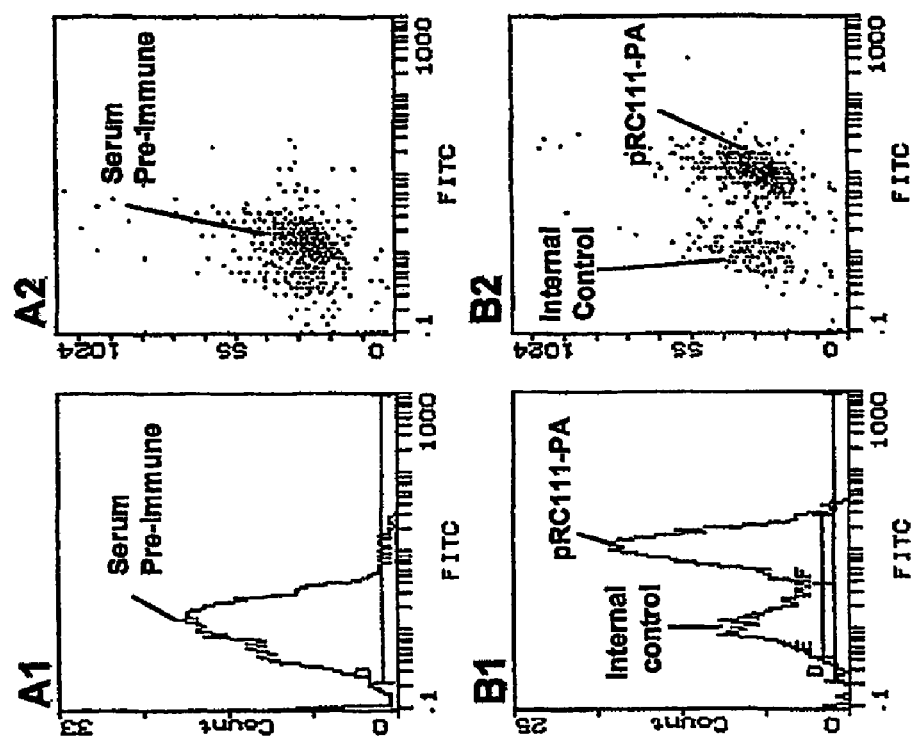

FIGS. 4(A1, A2, B1, B2): Reactivity of Abs induced by DNA vaccine containing VH-CDR3 region from patient PA with the patient tumor cells, as assessed by fluorescence activator cell sorting (FACS). Sera (diluted 1:50) from mice immunized with pRC111-PA were incubated with their target tumor cells (PA682). Results of a representative sample are displayed as peaks obtained with preimmune (FIG. 4A1 and FIG. 4A2) and immune serum (FIGS. 4B1 and B2).

FIG. 4: Reactivity of Abs induced by DNA vaccine containing VH-CDR3 region from patient PA with the patient tumor cells, as assessed by fluorescence activator cell sorting (FACS). The serum (diluted 1:50) from mice immunized with pRC111-PA was incubated with their target tumor cells (PA682) (A, B) or with tumor cells from patient BA (C).

The control serum was from the same pre-injected mice. After incubation, cells were washed and bound antibodies detected by FITC-conjugated goat anti-mouse serum, using a FACS-Scan. Results of a representative sample (PA) are displayed as peak presentations obtained with (FIGS. 4A1-A2) pre-immune and (FIGS. 4B1-B2) immune serum (6-weeks following pRC111-PA injection). The internal control peak (FIG. 4B1) shows the baseline reactivity of detecting goat fluoresceinated anti-mouse antibody alone. Table 3: FACS analysis of pRC111-PA antiserum challenged with BA tumor cells.

EXAMPLE 1

Molecular Rescue of VH-CDR3 Sequences from Patient Tumor B-Cells of Chronic Lymphoproliferative Disorders The aim of this study was to demonstrate the effectiveness of the short hypervariable region (VH-CDR3) of the idiotypic immunoglobulin, expressed on B-cells of chronic B-lymphoproliferative disorders, in allowing rapid cloning and specific immune response through naked DNA immunization.

Two EBV transformed cell lines (AS283A and PA682) derived from two non-Hodgkin's B-lymphoma patients' cells, and one frozen peripheral blood sample from a hairy-cell leukemia patient (BA), were used as sources of CDR3 sequences.

The WBC at diagnosis in the peripheral blood of the HCL-V patient was very high (130.000/mm$^3$) and the percentage of the leukemia cells >95%. The cell lines used as a source material for the CDR3 sequences were clonal cells whose origin from the primary lymphomas of the patients was previously established (Gaidano et al., In vitro establishment of AIDS-related lymphoma cell lines: phenotypic characterization, oncogene and tumor suppressor gene lesions and heterogeneity in Epstein-Barr virus infection. Leukemia, 7: 1621-1629, 1993).

The identity of their CDR3 regions with the sequences used for DNA vaccination was established by comparing the sequence of the amplified fragments obtained from the tumor cells with the sequence of the plasmids used for vaccination (see below). The same cells were also used to determine the presence of antibodies reactive with the idiotypes in treated mice (see below).

Total RNA was purified from patients' cells and cDNA prepared using random hexamers. The amplification was performed in two steps, as described, in the Example 2. The use of RNA and of a two step PCR procedure allowed high sensibility and specificity of yielded products.

Amplified variable regions and CDR3s were analyzed on a 2% SeaKem agarose gel (FMC, Rockland, Me.). Bands were purified by QIAEX gel extraction kit (Qiagen Inc., GmbH) according to manufacturer's instructions. The purified VH-CDR3 cDNAs were directly cloned into the NheI/NotI sites of one transcriptional cassette of pRC100-related plasmid vectors, with (pRC111) or without (pRC101) mouse IL2 (mIL2) cDNA in the second transcriptional cassette (Table 1) (Ciafrè et al. Plasmid, 40: 84-89, 1998). cDNA fragments were subsequently sequenced by dideoxy chain termination method using T7 DNA polymerase (Sequenase Version 2.0, USB).

Plasmid DNA was purified by Qiagen Plasmid Mega Kit (Cat. No. 12181) according to manufacturer's protocol, in order to avoid use of a mutagen (ethidium bromide) or CsCl gradient, both included in the standard protocol for plasmid purification. The DNA plasmid was resuspended at 1.2 ug/ul in sterile 225 mM NaCl (1.5×normal saline).

These multigenic vectors incorporate two different transcription cassettes controlled by two independent promoters (CMV and RSV promoters/enhancers) and allows co-expression of a cytokine, human IL2 or GM-CSF or a toxin, together with a specific antigen, the individual VH-CDR3 peptide (pRC111) (FIG. 1).

TABLE 1

DNA immunization constructs, encoded antigenic proteins and immune modulator

| | | Gene 1 | | | Gene 2 | | |
|---|---|---|---|---|---|---|---|
| Plasmid | Promoter | Cloning sites | Gene | Source | Promoter | Cloning sites | Cytokine |
| PRC100 | RSV | NheI-NotI | N | — | CMV | XhoI | N |
| PRC101 | RSV | NheI-NotI | VH-CDR3 | BA HCL | CMV | XhoI | N |
| PRC101 | RSV | NheI-NotI | VH-CDR3 | PA B-NHL | CMV | XhoI | N |
| PRC101 | RSV | NheI-NotI | VH-CDR3 | AS B-NHL | CMV | XhoI | N |
| PRC110 | RSV | NheI-NotI | N | — | CMV | XhoI | m IL2 |
| PRC111 | RSV | NheI-NotI | VH-CDR3 | BA HCL | CMV | XhoI | m IL2 |
| PRC111 | RSV | NheI-NotI | VH-CDR3 | PA B-NHL | CMV | XhoI | m IL2 |
| PRC111 | RSV | NheI-NotI | VH-CDR3 | AS B-NHL | CMV | XhoI | m IL2 |
| PRC112 | RSV | NheI-NotI | NS3 | HCV strain H | CMV | XhoI | m IL2 |

Abbreviations:
RSV=Rous sarcoma virus LTR promoter/enhancer; VH-CDR3=complementary determining region 3 of the variable immunoglobulin heavy chain; HCL=hairy cells leukemia; NHL=non-Hodgkin's B cell lymphoma; BA/PA/AS=patients CDR3 sources; CMV=cytomegalovirus promoter/enhancer; m IL2=murine interleukin 2; N=none; HCV=Hepatitis C virus; NS3=HCV non structural protein 3, 4403-4829 fragment

EXAMPLE 2

VH-CDR3 Amplification

The amplification was performed in two steps, using the following family specific PCR primers for human heavy chain CDR3 variable region: A) First step: Upstream: VH$_{1-3-5-7}$ 5'-(C,G)AG GTG CAG CTG GTG (C,G)AG TCT-3' (SEQ ID NO: 17); VH$_2$ 5'-CAG (G,A)TC ACC TTG AAG GAG TCT-3' (SEQ ID NO: 16); VH$_4$ 5'-CAG GTG CAG CTG CAG GAG TCG-3' (SEQ ID NO:15); VH$_6$ 5'-CAG GTA CAG CTG CAG CAG TCA-3' (SEQ ID NO: 14). Downstream: RHmu 5'-CAC GCT GCT CGT ATC CGA CGG-3' (SEQ ID NO:13). Upstream primers were derived from (Deane et al. Brit. J. Haematol., 77: 274-281, 1991).

Downstream primer RHmu was designed to anneal with the 5' terminus of the constant region mu of the human heavy chain. B).

Second step: Upstream: (eFR$_3$ derived) eFW$_3$ 5'-TTT G/CTAGC ATG CAC ACG GC(C,T) (G,C)TG TAT TAC TGT-3' (SEQ ID NO: 12). Downstream: (eLJH derived) eJH 5'-TAT GC/GGCCGC TTA TTA TGA GGA GAC GGT GAC C-3' (SEQ ID NO: 11). Upstream and downstream primers for the second step PCR were derived from (Ramasamy et al., Improved PCR method for detecting monoclonal immunoglobulin heavy-chain rearrangement in B-cell neoplasm. J. Clin. Pathol., 45: 770-775, 1992), with some modifications. As compared to published sequence, eJH annealing sequence (SEQ ID NO: 11) extends 2 nucleotide at 3' end of eLJH and eFW$_3$ annealing sequence (SEQ ID NO: 12) extends 1 nucleotide at 5' end of eFR$_3$, in order to improve specificity and PCR conditions. Moreover, both primers for the second step of PCR amplification included sequences for restriction sites (eFW$_3$, SEQ ID NO: 12: NheI; eJH: NotI) (underlined), preceded by a short sequence (italics) for enhancing enzymatic cleavage efficiency (Ausubel et al. *Current Protocols In Molecular Biology*. New York: Wiley J and Sons Inc., 1992). Insertion of NheI and NotI restriction sites as 5' flushing ends of the primers allowed the directional cloning of the amplified cDNAs in one transcriptional cassette of pRC110 vector (see below).

RNA was first isolated from cell lines and frozen clinical samples, as described (Chomczynski et al. Anal. Biochem., 162: 156-159, 1987). Synthesis of cDNA was performed using a first-strand cDNA synthesis kit (Perkin Elmer), MuLV Reverse Transcriptase (Perkin Elmer) and random hexamers in a 20 µl final volume; reaction conditions were 23° C. 10 minutes, 42° C. 45 minutes and 99° C. 5 minutes. RT-PCR was performed in a final volume of 100 µl with 15 pmol of each primer, 50 µmol of deoxynucleotide triphosphate and 1U of AmpliTAQ (Perkin Elmer); first step of amplification: 2 minutes at 96° C., followed by 5 cycles of 93° C. for 1 minute, 65° C. for 30 seconds, 72° C. for 30 seconds; and 30 cycles of 93° C. for 30 seconds, 65° C. for 30 seconds, 72° C. for 30 seconds. The second step of all PCRs (nested PCR) was performed with the hot-start procedure; reaction conditions were: 2 minutes at 96° C., followed by 10 cycles at 93° C. for 30 seconds, 65° C. for 30 seconds, 72° C. for 15 seconds, and 20 cycles of 15 seconds for each step of denaturation, annealing and polymerization.

The amplified fragments were sequenced by the dideoxy chain termination method using T7 DNA polymerase (Sequenase Version 2.0, USB). The CDR3 regions, the number of the somatic mutations present as well as the germline sequences of the patients from which the leukemia/lymphoma cells were derived, were established by comparing the sequence of the amplified fragments to the most homologous germline sequences of the Ig V genes present in the Genebank databases of the NCBI and in the V BASE sequence directory of the MRC Center for Protein Engineering (Cambridge, UK). The softwares used were, respectively, the BLAST program and the Mac Vector 6.0.1 software (Oxford Molecular Group PLC, Oxford, UK).

EXAMPLE 3

Animals and Immunization Protocols

Female Swiss mice about 8 weeks of age were used for immunization. Blood samples were obtained by tail bleeds, and serum was stored at −80° C. for subsequent assay. DNA injection was performed into the quadriceps muscle (intramuscular injection, i.m.) using a disposable, plastic insulin syringe and 29G×½" needle (Becton Dickinson, ref. No324804 micro-fine). Experimental groups received i.m. injections of 80 µg of pRC100 derived vectors encoding either only for CDR3 region (pRC101) or for mIL2 only (pRC110) or for both (pRC111) (FIG. 1 and Table 1).

As control two other groups of mice were injected, under the same experimental procedure, with empty plasmid (pRC100) or with pRC100 derived vector encoding for mIL2 and for an HCV non-structural antigen (NS-3) (pRC112). Two injections were performed respectively at the beginning of the experiment (T0) and three weeks after the first injection (T3). The third injection was performed 6 or 16 weeks after the beginning of experiments (T6 or T16). Mice were bled the day before each injection and at the following time points: T6, T9 and T19 (6, 9 and 19 weeks after the first injection, respectively).

EXAMPLE 4

Anti VH-CDR3 Antibody Detection

The production of antibodies by treated mice was assessed by FACS analysis, matching the sera with the EBV transformed B-cell lines (from patients PA and AS) or with thawed peripheral blood mononuclear cells (from patient BA), followed by incubation with fluorescein conjugated (FITC) goat anti-mouse antiserum (Coulter Clone, GAM-FITC) and detected by means of fluorescence activated flow cytometer (FACS) (Profile II FACS, Coulter). All staining steps were performed in PBS supplemented with FCS 5%, NHS 1% and NaN$_3$ 0.1% (staining medium). $2 \times 10^5$ cells were incubated 40 minutes in staining medium to reduce non specific binding, followed by a first step of staining with treated mouse serum diluted 1:50 or 1:20 in staining medium, in a final volume of 100 µl, 30 minutes on ice. After 3 washes in staining medium, $10^5$ cells were added as an internal control (only for PA and AS) and cells underwent a second step of staining with 1:500 FITC goat anti mouse serum in a final volume of 100 µl. After further 30 min, cells were washed thoroughly, resuspended in staining medium, and their fluorescence was read using a Profile II FACS.

When performed using serum samples obtained before the first immunization (T0), FACS analysis usually gives a single peak, in which the internal control and the double stained cells overlapped. Samples were selected as positive for anti-CDR3 antibody when two peaks were observed: the first one overlapped with that obtained with T0 sample and corresponded to the internal control (i.e. the cells that were added after the staining with the immune serum, usually ⅓ of total cells), while the second, high fluorescence peak was due to those cells that had undergone the staining with "immune" serum (⅔ of total cells). A fivefold higher mean fluorescence value for the "high fluorescence peak" with respect to the internal control was chosen as threshold value of positivity for anti-idiotypic antibody. For each individual mouse, all samples (T0-T19) were measured at the same time.

The specificity of the immune response developed against each individual VH-CDR3 sequence was evaluated matching sera from each group of animals with cells of the other patients and analyzed by FACS under the same technical protocol (e.g. sera from pRC111-PA injected mice were matched with BA and AS cells).

EXAMPLE 5

IL2 is Produced at the Site of Naked DNA Injection

In a preliminary trial, 8 two-months-old Swiss mice were intramuscularly (i.m.) injected both with pRC111-PA vector coding for mouse IL2 and VH-CDR3 from patient PA, and with empty pRC100 plasmid in the controlateral muscles as described in the Example 3. Transcription was evaluated at the site of injection by semi quantitative RT-PCR analysis, after 2 days and 1 week.

Total cellular RNA was extracted from excised muscles as described (Chomezynski P., et al., *Single step method of RNA isolation by acid guanidium thiocyanato-phenol-chloroform extraction*. Anal. Biochem., 162: 156-159, 1987). 500, 50 and 5 ng of total RNA were reverse transcribed using 500 ng oligo (dT) primers (GIBCO-BRL), 1 mM [dNTP] (Promega), 10 U AMV-RT (Promega) and 20 U RNAsin (Promega), in 20 µl final volume.

Incubation conditions were 42° C. 45 min., 99° C. 5 min. Mouse β-actin and mouse IL2 sequences were amplified using 5 µl of each cDNA preparation, 1U Taq polymerase (Promega), 2 mM $MgCl_2$ (Promega), 200 µM [dNTPs], 20 pmoles each primer, in 50 µl final volume. Mouse β-actin primers: FW: TGAGG CTCTT TTCCA GCCT (SEQ ID NO: 10); RV: CTAGA AGCAC TTGCG GTGCA (SEQ ID NO: 11).

Mouse IL2 primers: FW: CACTT CAAGC TCTAC AGCGG A (SEQ ID NO: 7); RV: AAAAT TTGAA GGTGA GCATC C (SEQ ID NO: 8). Amplification was performed by 38 cycles at 94° C. for 1 min., 56° C. for 1 min., 72° C. for 1 min.

Figure 3:
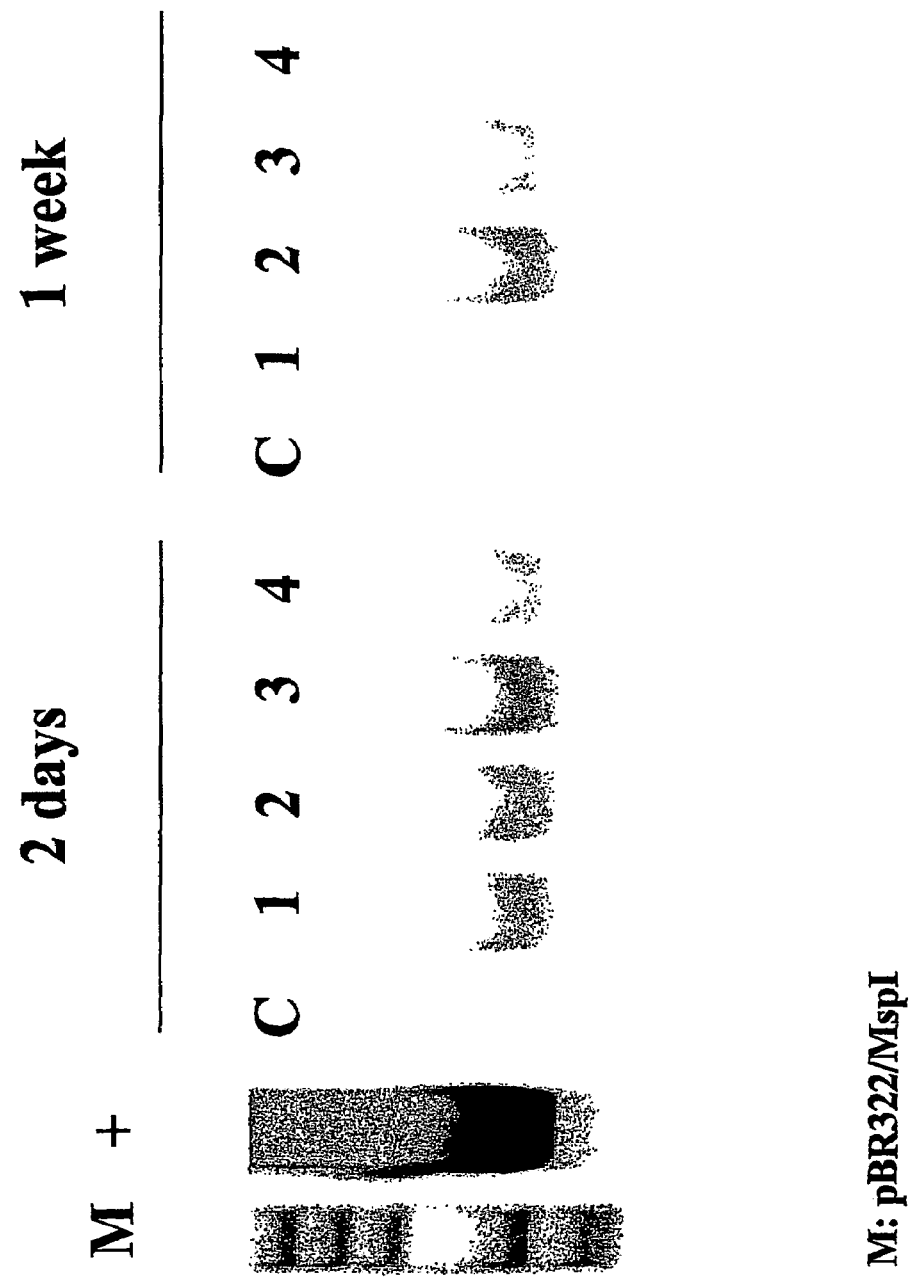

FIG. 3 shows results obtained in 4 animals (named 1, 2, 3, 4) 1 week following injection of, respectively, pRC111-PA in the left quadriceps muscle and pRC100 in the controlateral muscle (named C2 and C4). Even if to different extents, IL2 transcription was detected in all pRC111-PA injected muscles but no endogenous IL2 expression was demonstrated in pRC100 injected controlateral muscles. Same results were obtained at 2 days after injection (4 animals).

EXAMPLE 6

Naked DNA Injection of pRC111 Vectors Coding for the Individual VH-CDR3 Results in Immune Response Against the Idiotypic Ig Expressed on Patient's Tumor Cells Since human subjects that may potentially benefit from this therapeutic approach will have a broad range of MHC haplotypes, Swiss mice were chosen as test strain, given the fact that they are outbred and therefore display a variety of MHC haplotypes.

Thus, 8-week-old Swiss mice were i.m. injected with pRC101-PA (mIL2$^-$) or pRC111-PA (mIL2$^+$) vectors, in which VH-CDR3 from patient PA was cloned. As controls, three groups of mice were injected with either pRC100 (CDR3$^-$, mIL2$^-$ vector), or pRC110 (CDR3$^-$; mIL2$^+$ vector) (Ciafrè et al., A plasmid family containing two different expression cassettes suitable for immune modulation and genetic vaccination. Plasmid, 40: 8489, 1998) or pRC112 (encoding for HCV non-structural antigen NS-3, mIL2$^+$) (Papa et al., Development of a multigenic plasmid vector for HCV DNA immunization. Res. Virol. 149: 315-319, 1998) under the same experimental schedule, as described in the example 3.

At various time points after DNA injection, mouse were bled and the presence of anti-idiotypic antibodies was tested by means of cytofluorimetric analysis. For each individual mouse, all samples were measured at the same time.

FIG. 4 shows the FACS analysis obtained with PA682 cells (patient PA) challenged by pre-immune (4A) and immune (4B) serum samples of a mouse vaccinated with pRC111-PA vector.

We also evaluated the ability of naked DNA encoding for the VH-CDR3 region to induce anti-idiotypic antibodies, and observed the effect of mIL2 on this response. Only 20% of mice injected with pRC101-PA (IL2) produced measurable amounts of anti-idiotypic antibodies (Table 2). The injection of vector pRC111-PA (IL2$^+$) resulted in production of Ig-specific antibodies in 56% of mice. Thus, IL2 co-expressed with the antigen results in increase of efficiency of immunization. No specific antibodies were detected in mice injected with pRC100, pRC110 or pRC112 control vectors.

As shown in Table 2, the response was detected as early as 3 weeks after the first immunization, peaked soon after the second immunization and persisted over a considerably long span of time, since it was still detected after approximately five months. Furthermore, no decrease of titer of specific Igs was observed. As in the present experimental strategy, it is often found that a third injection of DNA did not always result in increase of the titer or of the number of animals that tested positive. Interestingly, the co-injection of IL2 increases the number of responding mice, but does not modify the kinetic of antibody production.

TABLE 2

Immune response evaluation against non-Hodgkin's lymphoma cells from patient PA.
Outbred Swiss mice were intramuscularly injected at T0, and 3 (T3) and 16 (T16) weeks later with different plasmid constructs. Sera were collected at 3 (T3), 6 (T6), 9 (T9), 16 (T16) and 19 (T19) weeks after the first injection. Lymphoma cells from patient PA were challenged by mouse sera and analyzed by FAC scanning. Results are expressed as percent of positive animals.

| Plasmid | mIL2 | Insert | N. | T3 | T6 | T9 | T16 | T19 |
|---|---|---|---|---|---|---|---|---|
| pRC 100 | − | − | 15 | 0 | 0 | 0 | 0 | 0 |
| pRC 100 | + | − | 15 | 0 | 0 | 0 | 0 | 0 |
| pRC 112 | + | HCV NS3 | 15 | 0 | 0 | 0 | 0 | 0 |
| pRC 101-PA | − | PA VH-CDR3 | 15 | 13 | 20 | 20 | 13 | 0 |
| pRC 101-PA | + | PA VH-CDR3 | 25 | 45 | 56 | 56 | 40 | 40 |

For abbreviations see Table 1

EXAMPLE 7

Anti CDR3 Responses can be Obtained with Different CDR3s

Two more points needed to be clarified in order to propose this approach for immunotherapy. The first was to demonstrate that such approach can be successful for several different VH-CDR3; the second was to show that the antibodies elicited really recognize a "private" epitope of the Ig, in order to minimize the possibility to generate a systemic self-reactive disease.

To address these points, in a new set of experiments the VH-CDR3 from 2 other patients (AS and BA) were cloned. Swiss mice were immunized with the resulting vectors pRC111-AS or BA, respectively, using the same protocol, as described in example 3. As it is shown in Table 3A, the rate of positive results obtained using 3 different CDR3s was similar. This observation confirmed that naked DNA immunization with vector pRC111 can result in anti-CDR3 response for several distinct CDR3s.

In order to address the second point, immune sera were also tested for ability to recognize cells obtained from the other patients (e.g., sera positive for anti CDR3-PA response were also matched with cells from patients AS and DA, and viceversa). This experiment allowed us to check the fine specificity of the antibody response. No cross reactivity towards the CDR3s different from the one used for immunization was found among sera that had tested positive (FIG. 4C and Table 3). This result confirms that no response against frame regions of the CDR3s was elicited using this protocol, and therefore that the risk of spreading of the immune response towards systemic self-reactivity is possibly low.

TABLE 3

Specificity of anti-VH-CDR3 immune response versus lymphoproliferative cells from three different patients (PA, AS, BA). Outbred Swiss mice were intramuscularly injected at T0, and 3 (T3) and 6 (T6) weeks later with different plasmid constructs. Sera were collected at 3 (T3), 6 (T6) and 9 (T9) weeks after the first injection. Results are expressed as percent of positive sera determined by FACS analysis.

| Plasmids | m IL2 | CDR3 | Patient's cells | Animals N. | Immune animals (%) | | |
|---|---|---|---|---|---|---|---|
| | | | | | T3 | T6 | T9 |
| A | | | | | | | |
| pRC 111-PA | + | PA | PA | 5 | 20 | 60 | 60 |
| pRC 111-AS | + | AS | AS | 5 | 0 | 40 | 40 |
| pRC 111-BA | + | BA | BA | 5 | NT | 40 | 40 |

TABLE 3-continued

Specificity of anti-VH-CDR3 immune response versus lymphoproliferative cells from three different patients (PA, AS, BA). Outbred Swiss mice were intramuscularly injected at T0, and 3 (T3) and 6 (T6) weeks later with different plasmid constructs. Sera were collected at 3 (T3), 6 (T6) and 9 (T9) weeks after the first injection. Results are expressed as percent of positive sera determined by FACS analysis.

| Plasmids | m IL2 | CDR3 | Patient's cells | Animals N. | Immune animals (%) | | |
|---|---|---|---|---|---|---|---|
| | | | | | T3 | T6 | T9 |
| B | | | | | | | |
| pRC 111-PA | + | PA | AS-BA | 5 | 0 | 0 | 0 |
| pRC 111-AS | + | AS | PA-BA | 5 | 0 | 0 | 0 |
| pRC 111-BA | + | BA | PA-AS | 5 | 0 | 0 | 0 |
| C | | | | | | | |
| pRC 110 | + | – | PA BA AS | 5 | 0 | 0 | 0 |

A = Percent of sera from mice injected with pRC111-PA/AS/BA vectors reacting with patient tumor cells expressing the same VH-CDR3 (PA/AS/BA).

B = Specificity of immune response against each VH CDR3. Sera from animals injected with vector encoding each idiotype were challenged with patients' cells expressing each of the three VH CDR3.

C = Control mice: sera from 5 mice injected with CDR3-free vector (pRC110) were challenged with patients' cells expressing each of the three VH CDR3.

NT = not tested.

---

The invention claimed is:

1. A therapeutic vaccine for a chronic B-lymphoproliferative disorder comprising a DNA segment coding for a hypervariable region (VH-CDR3) of the idiotypic immunoglobulin expressed on B-cells of a subject afflicted with a chronic B-lymphoproliferative disorder, wherein said DNA segment consists of an NheI-NotI DNA fragment of the DNA sequence amplified by eFW3 (SEQ ID NO:12) and eJH (SEQ ID NO:11) and wherein said DNA segment codes for amino acids His-Thr-Ala-Val-Tyr-Tyr-Cys (SEQ ID NO:18), a peptide having a length of 7-45 amino acids, and amino acids Val-Thr-Val-Ser-Ser (SEQ ID NO:19).

2. A vaccine according to claim 1 effective against a mammalian chronic B-lymphoproliferative disorder.

3. A vaccine according to claim 1 wherein said DNA segment is of mammalian origin.

4. A recombinant plasmid expression vector suitable for expression of a DNA segment in a mammal, said vector comprising a DNA segment coding for a hypervariable region (VH-CDR3) of a surface idiotypic immunoglobulin expressed on B-cells of chronic B-lymphoproliferative disorders, wherein said DNA segment in said vector consists of an NheI-NotI DNA fragment of the DNA sequence amplified by eFW3 (SEQ ID NO:12) and eJH (SEQ ID NO:11)

and wherein said DNA segment codes for amino acids His-Thr-Ala-Val-Tyr-Tyr-Cys (SEQ ID NO: 18), a peptide having a length of 7-45 amino acids, and amino acids Val-Thr-Val-Ser-Ser (SEQ ID NO:19).

5. A recombinant plasmid expression vector according to claim 4 wherein the hypervariable region (VH-CDR3) of the idiotypic immunoglobulin expressed on B-cells of chronic B-lymphoproliferative disorders is the only antigenic agent which is expressed in vivo when said vector is administered to a mammal as a vaccine composition.

6. A recombinant plasmid expression vector according to claim 4 wherein said vector is effective against a mammalian chronic B-lymphoproliferative disorder expressing a surface idiotypic immunoglobulin.

7. A recombinant plasmid expression vector according to claim 4 wherein said DNA segment is of mammalian origin.

8. A recombinant plasmid expression vector according to claim 4 wherein said plasmid expression vector also encodes an immunomodulatory molecule.

9. A recombinant plasmid expression vector according to claim 8 wherein said immunomodulatory molecule is selected from IL-2, GM-CSF, IL-12, IL-6, and fragments from bacterial immunotoxins.

10. A vaccine comprising the recombinant plasmid expression vector according to claim 4.

11. A vaccine composition effective against mammalian chronic B-lymphoproliferative disorders in which the surface idiotypic immunoglobulin is expressed, comprising a recombinant plasmid expression vector according to claim 4.

12. A vaccine composition according to claim 11 in a form suitable for parenteral administration.

13. A vaccine composition according to claim 12 in the form of an aqueous solution.

14. A vaccine composition according to claim 13 further containing an excipient and an adjuvant.

15. The vaccine of claim 2, wherein said disorder is a human disorder.

16. The vaccine of claim 3 wherein said DNA is of human origin.

17. The vector of claim 6 wherein said disorder is a human disorder.

18. The vector of claim 7 wherein said DNA is of human origin.

* * * * *

SEQUENCE LISTING

```
<160> NUMBER OF SEQ ID NOS: 19

<210> SEQ ID NO 1
<211> LENGTH: 36
<212> TYPE: PRT
<213> ORGANISM: Homo sapiens

<400> SEQUENCE: 1

Met His Thr Ala Val Tyr Tyr Cys Ala Lys Gly Ala Gln Gly Ala Ser
1               5                   10                  15

Leu Gly Lys Ala Tyr Phe Phe Asp Cys Trp Gly Gln Gly Thr Gln Val
            20                  25                  30

Thr Val Ser Ser
        35

<210> SEQ ID NO 2
<211> LENGTH: 31
<212> TYPE: PRT
<213> ORGANISM: Homo sapiens
```

```
<400> SEQUENCE: 2

Met His Thr Ala Val Tyr Tyr Cys Ala Arg Asn Lys Asp Asp Asp Ser
1               5                  10                  15

Pro Leu Glu Tyr Trp Gly Arg Gly Thr Leu Val Thr Val Ser Ser
            20                  25                  30

<210> SEQ ID NO 3
<211> LENGTH: 44
<212> TYPE: PRT
<213> ORGANISM: Homo sapiens

<400> SEQUENCE: 3

Met His Thr Ala Val Tyr Tyr Cys Ala Arg Val Leu Tyr Tyr Asp Phe
1               5                  10                  15

Trp Ser Gly Tyr Tyr Ile Ser Asn Tyr Tyr Tyr Tyr Gly Met Asp
            20                  25                  30

Val Trp Gly Gln Gly Thr Thr Val Thr Val Ser Ser
        35                  40

<210> SEQ ID NO 4
<211> LENGTH: 108
<212> TYPE: DNA
<213> ORGANISM: Homo sapiens

<400> SEQUENCE: 4
atgcacacgg ctgtgtatta ctgtgcgaag ggtgcgcagg gcgcatcact tggtaaggcc     60
tacttctttg actgctgggg ccagggaacc caggtcaccg tctcctca                 108

<210> SEQ ID NO 5
<211> LENGTH: 93
<212> TYPE: DNA
<213> ORGANISM: Homo sapiens

<400> SEQUENCE: 5
atgcacacgg ctgtgtatta ctgtgcgaga aataaggacg atgactcccc tcttgagtac     60
tggggccggg gaaccctggt caccgtctcc tca                                  93

<210> SEQ ID NO 6
<211> LENGTH: 132
<212> TYPE: DNA
<213> ORGANISM: Homo sapiens

<400> SEQUENCE: 6
atgcacacgg ctgtgtatta ctgtgcgaga gttttgtatt acgatttttg gagtggttat     60
tatatttcta attactacta ctactacggt atggacgtct ggggccaagg gaccacggtc    120
accgtctcct ca                                                        132

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
aaaatttgaa ggtgagcatc c                                               21

<210> SEQ ID NO 8
<211> LENGTH: 21
<212> TYPE: DNA
```

<213> ORGANISM: Artificial
<220> FEATURE:
<223> OTHER INFORMATION: primer

<400> SEQUENCE: 8
cacttcaagc tctacagcgg a                                              21

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
ctagaagcac ttgcggtgca                                                20

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
tgaggctctt ttccagcct                                                 19

<210> SEQ ID NO 11
<211> LENGTH: 33
<212> TYPE: DNA
<213> ORGANISM: Artificial
<220> FEATURE:
<223> OTHER INFORMATION: primer

<400> SEQUENCE: 11
tatgcggccg cttattatga ggagacggtg acc                                 33

<210> SEQ ID NO 12
<211> LENGTH: 33
<212> TYPE: DNA
<213> ORGANISM: Artificial
<220> FEATURE:
<223> OTHER INFORMATION: primer

<400> SEQUENCE: 12
tttgctagca tgcacacggc ystgtattac tgt                                 33

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
cacgctgctc gtatccgacg g                                              21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
caggtacagc tgcagcagtc a                                              21

```
<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
caggtgcagc tgcaggagtc g                                      21

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
cagrtcacct tgaaggagtc t                                      21

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
saggtgcagc tggtgsagtc t                                      21

<210> SEQ ID NO 18
<211> LENGTH: 7
<212> TYPE: PRT
<213> ORGANISM: Artificial
<220> FEATURE:
<223> OTHER INFORMATION: synthetic sequence

<400> SEQUENCE: 18

His Thr Ala Val Tyr Tyr Cys
1               5

<210> SEQ ID NO 19
<211> LENGTH: 5
<212> TYPE: PRT
<213> ORGANISM: Artificial
<220> FEATURE:
<223> OTHER INFORMATION: synthetic sequence

<400> SEQUENCE: 19

Val Thr Val Ser Ser
1               5
```